(12) United States Patent
Richter et al.

(10) Patent No.: US 7,151,151 B2
(45) Date of Patent: Dec. 19, 2006

(54) PREPARATION OF POLYISOCYANATES CONTAINING URETDIONE GROUPS

(75) Inventors: Frank Richter, Leverkusen (DE);
Reinhard Halpaap, Odenthal (DE);
Hans-Josef Laas, Gladbach (DE);
Andreas Hecking, Langenfeld (DE)

(73) Assignee: Bayer MaterialScience AG, Leverkusen (DE)

( * ) Notice: Subject to any disclaimer, the term of this patent is extended or adjusted under 35 U.S.C. 154(b) by 39 days.

(21) Appl. No.: 10/990,558

(22) Filed: Nov. 17, 2004

(65) Prior Publication Data

US 2005/0113551 A1    May 26, 2005

(30) Foreign Application Priority Data

Nov. 21, 2003   (DE) ................ 103 54 544

(51) Int. Cl.
*C08G 18/74* (2006.01)
(52) U.S. Cl. ............... 528/45; 528/73; 540/202
(58) Field of Classification Search ........... 540/202; 528/45, 73
See application file for complete search history.

(56) References Cited

U.S. PATENT DOCUMENTS

| | | | |
|---|---|---|---|
| 3,645,979 A | 2/1972 | Liebsch et al. | 260/77.5 NC |
| 4,476,054 A | 10/1984 | Disteldorf et al. | 260/239 A |
| 4,614,785 A | 9/1986 | Richter et al. | 528/45 |
| 4,912,210 A | 3/1990 | Disteldorf et al. | 540/202 |
| 4,929,724 A | 5/1990 | Engbert et al. | 540/202 |
| 5,750,629 A | 5/1998 | Laas et al. | 528/45 |
| 2002/0028930 A1 | 3/2002 | Laas et al. | 540/202 |
| 2004/0106789 A1 | 6/2004 | Richter et al. | 540/202 |

FOREIGN PATENT DOCUMENTS

| | | |
|---|---|---|
| DE | 1 025 487 | 3/1958 |
| DE | 1 934 763 | 1/1971 |
| EP | 780 37 | 6/1997 |
| GB | 1 153 815 | 5/1969 |
| GB | 1 244 416 | 9/1971 |

OTHER PUBLICATIONS

J. Prakt Chem., 336, (month unavailable) 1994, pp. 185-200, Hans Josef Laas et al, Zur Synthese aliphatischer Polyisocyanate-Lackpolyisocyanate mit Biuret-, Isocyanurat- oder Uretdionstruktur.

*Primary Examiner*—Rachel Gorr
(74) *Attorney, Agent, or Firm*—Joseph C. Gil; Lyndanne M. Whalen; N. Denise Brown (57) ABSTRACT

A method of dimerizing isocyanates including reacting the isocyanates in the presence of phosphines containing at least one directly phosphorus-attached bicyclic, cycloaliphatic radical. The polyisocyanate compositions obtained as described above can be used in mouldings, coating materials, adhesives, sealants or adjuvants that further include the polyisocyanate compositions and one or more materials selected from antioxidants, light stabilizers, pigments, fillers, additives, levelling assistance, defoamers and matting agents. The coating materials, adhesives or sealants can be used to coat substrates.

6 Claims, 3 Drawing Sheets

PREPARATION OF POLYISOCYANATES CONTAINING URETDIONE GROUPS

CROSS REFERENCE TO RELATED PATENT APPLICATION

The present patent application claims the right of priority under 35 U.S.C. §119 (a)–(d) of German Patent Application No. 103 54 544.1, filed Nov. 21, 2003.

BACKGROUND OF THE INVENTION

1. Field of the Invention

The invention relates to the use of specific cycloalkylphosphines as catalysts for isocyanate dimerization (uretdione formation) and to a process for preparing polyisocyanates with a high uretdione group content.

2. Description of the Prior Art

Aliphatic isocyanates which contain uretdione groups and are based on optionally branched, linear aliphatic diisocyanates are distinguished by a particularly low viscosity. Products based on cycloaliphatic diisocyanates are generally highly viscous or solid substances which can be used as internally blocked crosslinkers, free from elimination products, in coating systems.

An overview of isocyanate oligomerization is given in J. Prakt. Chem./Chem. Ztg. 1994, 336, 185–200.

Tris(dialkylamino)phosphines (DE-A 3 030 513) optionally in conjunction with co-catalysts (DE-A 3 437 635) exhibit good selectivity for the formation of uretdione groups (uretdione selectivity). Their technical usefulness is hindered, however, by the serious imperfection represented by the high carcinogenic potential of their phosphorus oxides, e.g. hexamethylphosphoric triamide.

DE-A 3 739 549 discloses the catalytic NCO dimerization with 4-dialkylaminopyridines, such as 4-dimethylaminopyridine (DMAP), but the formation of uretdione is selected only in the case of specific cycloaliphatic isocyanates such as isophorone diisocyanate (IPDI). Linear aliphatic isocyanates such as hexamethylene diisocyanate (HDI) and also branched, linear aliphatic isocyanates such as trimethylhexane diisocyanate (TMDI) and methylpentane diisocyanate (MPDI), when used with DMAP and related compounds, give heterogeneous reaction products which are predominantly highly coloured.

DE-A 1 670 720 discloses the preparation of aliphatic polyisocyanates containing uretdione groups, in which the catalysts used are tertiary phosphines having at least one aliphatic substituent and also boron trifluoride and its adducts. It is noted that high fractions of uretdione groups in the product can be obtained only at low conversions and at reaction temperatures between 50 and 80° C., with the accompanying formation of isocyanate trimers (isocyanurates and iminooxadiazinediones) and also, particularly at a relatively high temperature, of other by-products such as carbodiimides or uretonimines. Uretonimines are especially disruptive since they tend to give off monomeric isocyanate in the course of storage.

The German patent application with the application number DE-1 025 487 8, hitherto unpublished at the priority date of the present specification, describes the use of phosphines containing at least one cycloaliphatic, P-attached radical as catalysts for NCO dimerization. The catalysts are distinguished by a substantially higher uretdione selectivity as compared with other trialkylphosphines of the prior art.

SUMMARY OF THE INVENTION

The present invention is directed to a method of dimerizing isocyanates including reacting the isocyanates in the presence of phosphines containing at least one directly phosphorus-attached bicyclic, cycloaliphatic radical.

Embodiments of the present invention also provide a process for dimerizing isocyanates that includes reacting a mixture that contains
a) at least one organic isocyanate having an NCO functionality $\geq 2$,
b) a catalyst comprising at least one phosphine containing at least one directly phosphorus-attached bicyclic, cycloaliphatic radical, and
c) optionally solvents.

The present invention also provides polyisocyanate compositions obtained by the processes described above as well as mouldings, coating materials, adhesives, sealants or adjuvants that include the above-described polyisocyanate compositions one or more materials selected from antioxidants, light stabilizers, pigments, fillers, additives, levelling assistance, defoamers and matting agents.

The present invention also provides substrates coated with one or more of the above-described coating materials, adhesives or sealants.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about."

It has now been found that phosphines which contain at least one directly phosphorus-attached bicyclic, cycloaliphatic radical are likewise highly suitable as catalysts for the selective formation of uretdione (isocyanate dimerization). Furthermore, the phosphines essential to the invention have a higher selectivity and longer catalyst life, for a given number of cyclic P-attached substituents, than their analogues having monocyclic substituents.

The invention provides for the use of phosphines containing at least one, directly phosphorus-attached bicyclic, cycloaliphatic radical in the dimerization of isocyanates.

Preferred phosphines for isocyanate dimerization correspond to the formula where R$^1$ is an optionally singly or multiply $C_1$–$C_{12}$ alkyl- or alkoxy-substituted, bicyclic, cycloaliphatic $C_4$–$C_{20}$ radical and R$^2$, R$^3$ independently of one another is an optionally singly or multiply $C_1$–$C_{12}$ alkyl- or alkoxy-substituted mono- or bicyclic, cycloaliphatic $C_4$–$C_{20}$ radical or a linear or branched aliphatic $C_1$–$C_{20}$ radical.

Preferred compounds of the formula I are those in which R$^1$ is a singly or multiply $C_1$–$C_{12}$ alkyl-substituted norbornyl radical (=2,2,1-bicycloheptyl radical) and R$^2$ is alternatively identical to R$^1$ or to R$^3$, R$^3$ being a singly or multiply $C_1$–$C_8$ alkyl-substituted, aliphatic $C_1$–$C_{12}$-alkyl radical.

Examples of phosphines for use in accordance with the invention are: norbornyl-dime-thylphosphine, norbornyl-diethylphosphine, norbornyl-di-n-propylphosphine, norbornyl-di-isopropylphosphine, norbornyl-dibutylphosphine, where 'butyl' can stand for all isomers, i.e. n-butyl, iso-butyl, 2-butyl, tert-butyl and cyclo-butyl, norbornyl-dihexylphosphine (all isomeric hexyl radicals), norbornyl-dioctylphosphine (all isomeric octyl radicals), dinorbornyl-methylphosphine, dinorbornyl-ethylphosphine, dinorbornyl-n-propylphosphine, dinorbornyl-isopropylphosphine, dinorbornyl-butylphosphine (all isomeric butyl radicals), dinorbornyl-hexylphosphine (all isomeric hexyl radicals), dinorbornyl-octylphosphine (all isomeric octyl radicals), trinorbornylphosphine, dimethyl-(1,7,7-trimethyl-bicyclo[2.2.1]hept-2-yl)-phosphine, diethyl-(1,7,7-trimethyl-bicyclo[2.2.1]hept-2-yl)-phosphine, di-n-propyl-(1,7,7-trimethyl-bicyclo[2.2.1]hept-2-yl)-phosphine, di-iso-propyl-(1,7,7-trimethyl-bicyclo[2.2.1]hept-2-yl)-phosphine, dibutyl-(1,7,7-trimethyl-bicyclo[2.2.1]hept-2-yl)-phosphine (all isomeric butyl radicals), dihexyl-(1,7,7-trimethyl-bicyclo[2.2.1]hept-2-yl)-phosphine (all isomeric hexyl radicals), dioctyl-(1,7,7-trimethyl-bicyclo[2.2.1]hept-2-yl)-phosphine (all isomeric octyl radicals), methyl-bis-(1,7,7-trimethyl-bicyclo[2.2.1]hept-2-yl)-phosphine, ethyl-bis-(1,7,7-trimethyl-bicyclo[2.2.1]hept-2-yl)-phosphine, n-propyl-bis-(1,7,7-trimethyl-bicyclo[2.2.1]hept-2-yl)-phosphine, iso-propyl-bis-(1,7,7-trimethyl-bicyclo[2.2.1]hept-2-yl)-phosphine, butyl-bis-(1,7,7-trimethyl-bicyclo[2.2.1]hept-2-yl)-phosphine (all isomeric butyl radicals), hexyl-bis-(1, 7,7-trimethyl-bicyclo[2.2.1]hept-2-yl)-phosphine (all isomeric hexyl radicals), octyl-bis-(1,7,7-trimethyl-bicyclo[2.2.1]hept-2-yl)-phosphine (all isomeric octyl radicals), dimethyl-(2,6,6-trimethyl-bicyclo[3.1.1]hept-3-yl)-phosphine, diethyl-(2,6,6-trimethyl-bicyclo[3.1.1]hept-3-yl)-phosphine, di-n-propyl-(2,6,6-trimethyl-bicyclo[3.1]-hept-3-yl)-phosphine, di-iso-propyl-(2,6,6-trimethyl-bicyclo[3.1.1]hept-3-yl)-phosphine, dibutyl-(2,6,6-trimethyl-bicyclo[3.1.1]hept-3-yl)-phosphine (all isomeric butyl radicals), dihexyl-(2,6,6-trimethyl-bicyclo[3.1.1]hept-3-yl)-phosphine (all isomeric hexyl radicals), dioctyl-(2,6,6-trimethyl-bicyclo[3.1.1]hept-3-yl)-phosphine (all isomeric octyl radicals), methyl-bis-(2,6,6-trimethyl-bicyclo[3.1.1]hept-3-yl)-phosphine, ethyl-bis-(2,6,6-trimethyl-bicyclo[3.1.1]hept-3-yl)-phosphine, n-propyl-bis-(2,6,6-trimethyl-bicyclo[3.1.1]hept-3-yl)-phosphine, iso-propyl-bis-(2,6,6-trimethyl-bicyclo[3.1.1]hept-3-yl)-phosphine, butyl-bis-(2,6,6-trimethyl-bicyclo[3.1.1]hept-3-yl)-phosphine (all isomeric butyl radicals), hexyl-bis-(2,6,6-trimethyl-bicyclo[3.1.1]hept-3-yl)-phosphine (all isomeric hexyl radicals), and octyl-bis-(2,6,6-trimethyl-bicyclo[3.1.1]hept-3-yl)-phosphine (all isomeric octyl radicals).

These can be used as catalyst for uretdione formation individually, in any desired mixtures with one another or in mixtures with other primary, secondary and/or tertiary alkyl-, aralkyl- and/or arylphosphines.

The invention further provides a process for preparing polyisocyanates containing uretdione groups, in which a) at least one organic isocyanate having an NCO functionality ≧2, b) a catalyst comprising at least one phosphine for use in accordance with the invention, c) optionally solvents and d) optionally additives are reacted.

The amount of the catalyst for use in the process of the invention is guided primarily by the target reaction rate and is situated in the range from 0.01 to 5 mol %, based on the sum of the molar amounts of the isocyanate used and of the catalyst. It is preferred to use from 0.05 to 3 mol % of catalyst.

In the process of the invention the catalyst b) can be used neat or in solution in solvents. Suitable solvents in this context include all compounds which do not react with phosphines, such as aliphatic or aromatic hydrocarbons, alcohols, ketones, esters and ethers, for example. Preferably the phosphines are used neat in the process of the invention.

As isocyanates for use in accordance with the invention in a) it is possible in principle to use all known isocyanates, prepared by phosgenation or by phosgene-free processes, individually or in any desired mixtures with one another.

Preference is given to the use of aliphatic, cycloaliphatic or araliphatic di- or polyisocyanates with an NCO functionality ≧2.

Particular preference is given to the use of optionally branched, aliphatic diisocyanates optionally containing cyclic radicals and having isocyanate groups attached to a primary carbon atom. Examples thereof are pentane diisocyanate, hexane diisocyanate, heptane diisocyanate, octane diisocyanate, nonane diisocyanate, decane diisocyanate, undecane diisocyanate and dodecane diisocyanate, it being possible to employ any desired isomers of the aforementioned compounds.

Very particular preference is given to using hexamethylene diisocyanate (HDI), methylpentane diisocyanate (MPDI), trimethylhexane diisocyanate (TMDI), bis(isocyanatomethyl)cyclohexane (H$_6$XDI) and norbornane diisocyanate (NBDI) individually or in any desired mixtures with one another.

Additionally it is possible to use isophorone diisocyanate (IPDI), bis(isocyanatocyclohexyl)methane (H$_{12}$MDI), bis(isocyantomethyl)benzene (xylylene diisocyanate, XDI) and bis(2-isocyantoprop-2-yl)benzene (tetramethylxylylene diisocyanate, TMXDI) in the process of the invention.

The process of the invention is conducted such that the conversion of the NCO groups is from 5 to 90%, preferably from 10 to 60%, more preferably from 10 to 50%.

The process of the invention is carried out in the temperature range from 0° C. to 150° C., preferably 0° C. to 80° C., more preferably 0° C. to 60° C., in particular 0° C. to 40° C.

In order to achieve NCO group conversions in accordance with the above ranges the reaction is terminated at the desired degree of conversion.

Catalyst poisons suitable for terminating the reaction after the desired degree of conversion has been achieved include in principle all of those hitherto described (DE-A 1670667, 1670720, 1934763, 1954093, 3437635, U.S. Pat. No. 4,614, 785) such as alkylation agents (e.g. dimethyl sulphate, methyl toluenesulphonate), organic or inorganic peroxides, acid chlorides and also sulphur, which are reacted with the catalyst with an increase in temperature where appropriate (version A; cf. also Examples 1 to 6).

Following the deactivation of the reaction mixture in accordance with version A it is possible for unreacted monomer and/or the deactivated catalyst to be separated off.

The process can also be carried out without chemical deactivation of the catalyst. For that purpose, immediately after the desired conversion has been reached, the active catalyst is separated off from the reaction mixture in order to prevent further reaction with the formation, possibly, of by-product. (version B).

At the same time as, or else after, the catalyst is separated off it is possible for unreacted residual monomer from the reaction mixture treated in accordance with version B to be separated off.

In the process of the invention unreacted monomers, the catalyst and/or other unwanted components can be separated off from the reaction mixture using all known separation techniques, such as distillation, extraction or crystallization/filtration, for example. Preference is given to distillation, where appropriate in the specific embodiment of thin-film distillation. It is of course also possible to employ combinations of two or more of these techniques.

For terminating the reaction in accordance with version B it is preferred to remove the catalyst by distillation, in which case it is possible where appropriate to remove unreacted monomer at the same time.

In the course of the working-up of a reaction terminated in accordance with version A or B the residual monomer present is preferably removed by distillation.

Where the polyisocyanate prepared in accordance with the invention is intended still to contain free, unreacted monomer, such as is of interest, for example, for its further processing to NCO-blocked products or low-NCO or NCO-free polyuretdione curatives, for the powder coating sector, for example, it is possible to forego the separation of monomer after the termination of the reaction (versions A and B).

For the conduct of the process of the invention it is irrelevant whether the process is carried out in whole or in part batchwise or continuously.

Additionally it is possible in the process of the invention to add stabilizers and additives which are customary in polyisocyanate chemistry, at any desired point in time. Examples are antioxidants, such as sterically hindered phenols (2,6-di-tert-butylphenol, 4-methyl-2,6-di-tert-butylphenol), light stabilizers, such as HALS amines, triazoles, etc., weak acids or catalysts for the NCO—OH reaction, such as dibutyltin dilaurate (DBTL).

It may additionally be sensible to add small amounts of a catalyst poison for use in version A to a product worked up in accordance with version B, in order to increase the reverse cleavage stability and to reduce the propensity for by-products to be formed, for discoloration and/or for the free NCO groups to react further, in the course of product storage, for example.

Products prepared by the process of the invention and based on optionally branched, linear aliphatic di- or polyisocyanates, containing no cycloalkyl substituents, are light in colour and have a viscosity <1000 mPas/23° C. If cycloaliphatic and/or araliphatic di- or polyisocyanates are used the resins obtained range from highly viscous to solid (viscosity >10 000 mPas/23° C.).

In low-monomer form, i.e. after the removal of unreacted monomer, the products of the invention have an NCO content <27.3% by weight, preferably <25% by weight.

The polyisocyanates prepared for the process of the invention serve as starting materials for producing, for example, mouldings (foamed where appropriate), paints, coating materials, adhesives, sealants or adjuvants, it being possible where appropriate for the free, non-uretdionized NCO groups to have been blocked.

Methods suitable for blocking the free, non-uretdionized NCO groups include all of those which are known to the person skilled in the art. As blocking agents it is possible in particular to use phenols (e.g. phenol, nonylphenol, cresol), oximes (e.g. butanone oxime, cyclohexanone oxime), lactams (e.g. □-caprolactam), secondary amines (e.g. diisopropyl-amine), pyrazoles (e.g. dimethylpyrazole), imidazoles, triazoles) or malonic and acetic esters.

The substantially by-product-free polyisocyanates containing uretdione groups that are prepared by the process of the invention can be used in particular for preparing one- and two-component polyurethane coating materials, in mixtures where appropriate with other, prior art di- or polyisocyanates, such as di- or polyisocyanates containing biuret, urethane, allophanate, isocyanurate, and iminooxadiazinedione groups.

Likewise particularly preferred is the use of the polyisocyanates prepared in accordance with the invention on the basis of optionally branched, linear aliphatic isocyanates as reactive diluents for reducing the viscosity of polyisocyanate resins of relatively high viscosity.

For the reaction of the polyisocyanates prepared in accordance with the invention to form the polyurethane it is possible to use any compounds having at least two isocyanate-reactive functionalities, individually or in any desired mixtures with one another (isocyanate-reactive binder).

Preference is given to using one or more isocyanate-reactive binders which are known per se in polyurethane chemistry, such as polyhydroxy compounds or polyamines. As polyhydroxy compounds it is particularly preferred to use polyester-, polyether-, polyacrylate- and/or polycarboxylic acid-polyols, where appropriate with the addition of low molecular mass polyhydric alcohols as well.

The equivalents ratio between nonuretdionized isocyanate group, which where appropriate may have also have been blocked, and isocyanate-reactive functionality of the isocyanate-reactive binder, such as OH—, NH— or COOH, is from 0.8 to 3, preferably from 0.8 to 2.

A possibility is the use of an excess of isocyanate-reactive binder, since the cleavage of the uretdione ring, where appropriate at elevated temperature and/or with addition of catalyst, leads to the liberation of further NCO groups, which are able to react with the excess of isocyanate-reactive functionalities. As a result, the network density of the polymer formed is increased and its properties are advantageously influenced.

For accelerating the crosslinking reaction of the polyisocyanates prepared in accordance with the invention with the isocyanate-reactive binder it is possible to use any of the catalysts known from polyurethane chemistry. By way of example use may be made of metal salts such as dibutyltin (IV) dilaurate, tin(II) bis(2-ethylhexanoate), bismuth(III) tris(2-ethylhexanoate), zinc(II) bis(2-ethylhexanoate) or zinc chloride and also tertiary amines such as 1,4-diazabicyclo[2.2.2]octane, triethylamine or benzyldimethylamine.

At the formulation stage the optionally blocked polyisocyanate prepared in accordance with the invention, the isocyanate-reactive binder, catalyst(s) and, where used, the usual extras such as pigments, fillers, additives, levelling assistance, defoamers and/or matting agents are mixed with one another and homogenized in a customary mixing unit such as, for example, a sand mill, where appropriate with the use of solvents.

Suitable solvents include all customary paint solvents known per se, such as ethyl and butyl acetate, ethylene or propylene glycol monomethyl, monoethyl or monopropyl ether acetate, 2-butanone, 4-methyl-2-pentanone, cyclohexanone, toluene, xylene, solvent naphtha, N-methylpyrrolidone, etc.

The coating materials can be applied in solution or from the melt and also, where appropriate, in solid form (powder coating materials) by the customary methods such as spreading, rolling, pouring, spraying or dipping, by the fluid-bed sintering method or by electrostatic spraying processes, for example, to the article that is to be coated.

Suitable substrates include all known materials of construction, especially metals, wood, plastics and ceramic.

EXAMPLES

All percentages are to be understood as percentages by weight unless noted otherwise.

The determination of the NCO content of the resins described in the inventive and comparative examples was made by titration in accordance with DIN 53 185.

The dynamic viscosities were determined at 23° C. using the VT 550 viscometer from Haake, Karlsruhe, Del. Measurements were made at different shear rates in order to ensure that the rheology of the described polyisocyanates prepared in accordance with the invention and that of the comparison products corresponds to that of ideal Newtonian liquids. Accordingly it is unnecessary to state the shear rate.

The indication 'mol %' or 'molar ratio of different types of structure to one another' is based on NMR spectroscopy measurements. It refers in each case, unless otherwise specified, to the sum of the types of structure formed by the modification reaction (oligomerization) from the previously free NCO groups of the isocyanate to be modified.

$^{13}$C-NMR measurements were made on the instruments DPX 400, AVC 400 or DRX 700 from Bruker, Karlsruhe, Del. and on approximately 50% samples in dry CDCl$_3$ or on approximately 80% samples in D$_6$-DMSO ($^{13}$C-NMR: 100 or 176 MHz, relaxation delay: 4 sec, at least 2000 scans). The reference chosen for the ppm scale comprised small amounts of tetramethylsilane in the corresponding solvent ($\delta$=0 ppm) or the solvent itself ($\delta$=77.0 ppm (CDCl$_3$) or $\delta$=43.5 ppm (D$_6$-DMSO)).

Unless indicated otherwise, the reactions were carried out using freshly degassed HDI as starting material. The term 'freshly degassed' means here that the HDI used had been freed from dissolved gases immediately prior to catalytic reaction, by stirring under reduced pressure (<1 mbar) for at least 30 minutes, and then blanketed with nitrogen.

All reactions were carried out under an atmosphere of dry nitrogen.

Norbornyl-substituted and di-norbornyl-substituted phosphines were prepared by methods known from the literature (J. Org. Chem., 1961, 26, 5138–5145) by free-radical addition reaction of 1-olefins with norbornylphosphine (bicyclo [2.2.1]hept-2-yl-phosphane; nbPH$_2$) or with di-norbornylphosphine (bis-bicyclo[2.2.1]hept-2-yl-phosphane; nb$_2$PH). It is of course also possible to start from alkyl- or dialkylphosphines and norbornene (bicyclo[2.2.1]hept-2-ene).

Preparation of Norbornyl-diethylphosphine (nbPEt$_2$)

A 1.51 stirred autoclave was charged at room temperature and under nitrogen with 108 g of a 50% strength solution of norbornylphosphine in toluene (Cytec Canada Inc., Ontario, Calif.), 3.2 g of azobisisobutyronitrile (AIBN) and 25 ml of toluene. Then 32 g of ethylene were metered in and the mixture was heated to 80° C. with stirring. After the pressure had fallen from 30 bar at the start to 13 bar over 3 h, the autoclave was cooled to room temperature and let down. Subsequently a further 1.6 g of AIBN in solution in 40 ml of toluene and 32 g of ethylene were added and the mixture was heated at 70° C. for 5 h, with stirring. The reaction mixture was then worked up by distillation under a high vacuum to give 52 g (95% of theory; b.p.: 52–54° C. at 0.006 mbar) of nbPEt$_2$.

Norbornyl-dibutylphosphine (nbPBu$_2$, b.p.: 95° C. at 0.01 mbar) and dinorbornyl-ethyl-phosphine (nb$_2$PEt, b.p.: 125° C. at 0.1 mbar) were obtained analogously. In the case of the higher homologues norbornyl-dihexylphosphine (nbPHex$_2$, b.p.: 150° C. at 0.01 mbar), norbornyl-didecylphosphine (nbPDec$_2$, b.p.: 200° C. (bath temperature in bulb tube distillation) at 0.003 mbar) and dinorbornyl-decylphosphine (nb$_2$PDec, b.p.: 190° C. (bath temperature in bulb tube distillation) at 0.03 mbar) it was possible to operate at atmospheric pressure, since the boiling points of the corresponding olefins (1-hexene and 1-decene, respectively) at atmospheric pressure were high enough to produce sufficiently rapid decomposition of the AIBN to initiate the free-radical chain reaction.

Examples 1 to 6

Inventive 10 g portions of freshly degassed HDI were stirred under nitrogen in glass vessels sealed with septa in the presence of the amounts indicated in Tables 1 to 6 of the catalyst specified therein, at the stated temperatures, using a magnetic stirrer core, and the progress of the reaction was examined at regular intervals by measuring the refractive index (at 20° C. and the frequency of the light of the D line of the sodium spectrum, $n_D^{20}$) of the reaction mixture (start=no conversion=$n_D^{20}$ of the pure HDI=1.4523).

Figure 2:
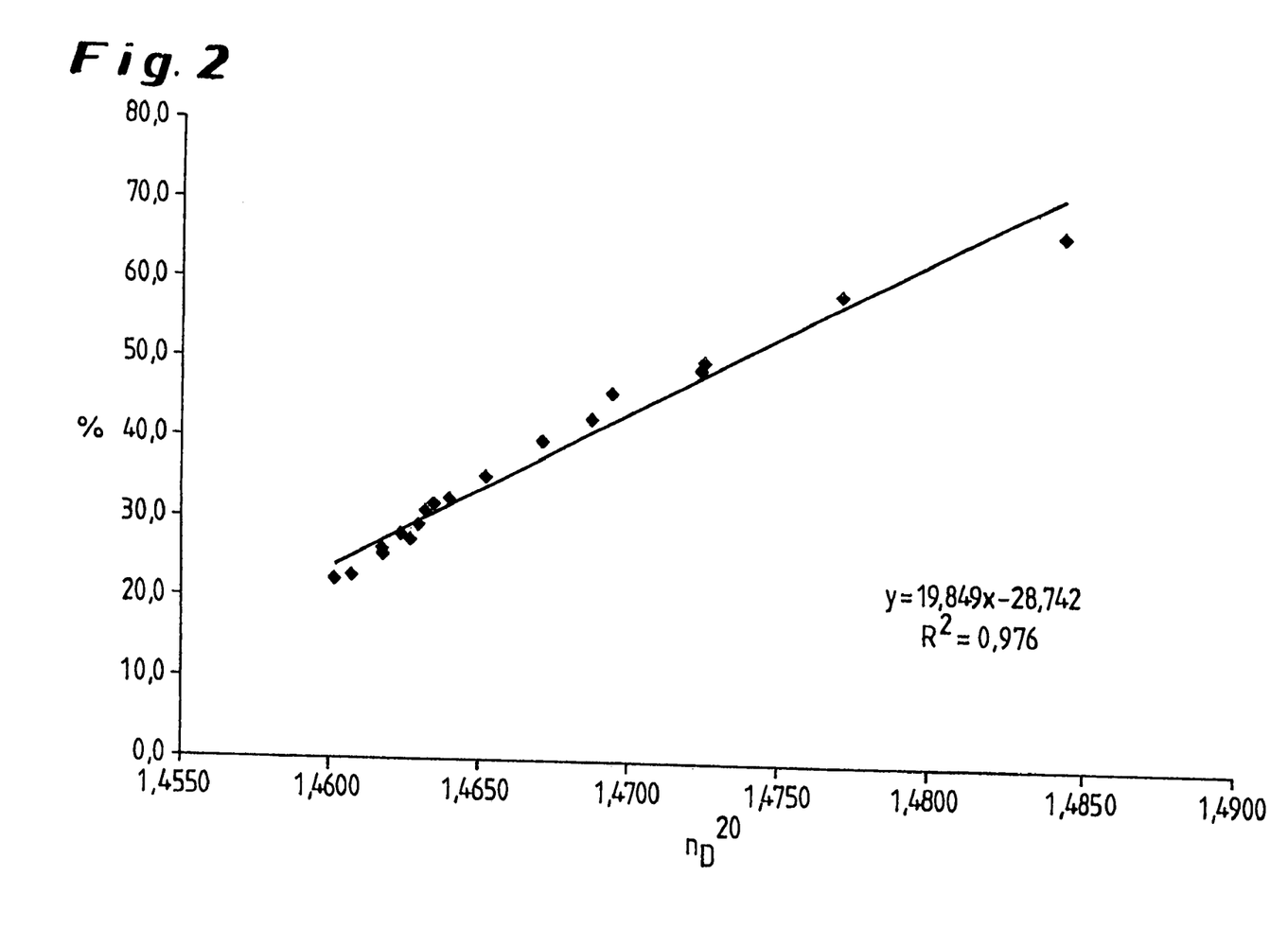
FIG. 2 shows a graph depicting the relationship between conversion and $n_D^{20}$ of a reaction mixture according to the invention.

The correlation between the variables of conversion (yield) and $n_D^{20}$ of the reaction mixture is virtually linear in the yield range up to about 60% uretdione polyisocyanate resin in the reaction mixture (cf. Example 7 and FIG. 2). The relationship between conversion and $n_D^{20}$ of the reaction mixture that is depicted in Example 7 was used to calculate the conversion for the samples under discussion here; for that purpose the refractive index measured was inserted into the following formula $$\text{Conversion}[\%] = 19.849 * n_D^{20} - 28.742$$

and the conversion was calculated.

Prior to the determination of selectivity the conversion samples had elemental sulphur added to them in order to prevent further reaction, the quantity of sulphur corresponding to their phosphine content, and they were subjected to analysis by NMR spectroscopy. For a clearer overview of the selectivities the parameter U/T was defined as the molar ratio of the uretdione structures relative to the sum of the two trimer structures (iso-cyanurate and iminooxadiazinedione).

TABLE 1

Catalyst: nbPHex$_2$ (0.3 mol %, based on HDI)
Reaction temperature: 40° C.

| Reaction time [hh:mm] | $n_D^{20}$ | HDI conversion [%] | U/T |
|---|---|---|---|
| 01:02 | 1.4528 | 9% | 14.2 |
| 03:28 | 1.4539 | 12% | 9.9 |
| 07:38 | 1.4554 | 15% | 8.8 |
| 23:08 | 1.4589 | 22% | 7.6 |
| 32:00 | 1.4599 | 24% | 7.7 |

TABLE 2

Catalyst: nbPHex$_2$ (0.3 mol %, based on HDI)
Reaction temperature: 60° C.

| Reaction time [hh:mm] | $n_D^{20}$ | HDI conversion [%] | U/T |
|---|---|---|---|
| 01:45 | 1.4536 | 11% | 14.6 |
| 03:45 | 1.4548 | 13% | 13.1 |
| 05:45 | 1.4562 | 16% | 12.1 |
| 21:10 | 1.4632 | 30% | 7.8 |
| 29:25 | 1.4655 | 35% | 6.8 |
| 45:40 | 1.4688 | 41% | 5.5 |
| 69:35 | 1.4706 | 45% | 5.0 |

TABLE 3

Catalyst: nbPHex$_2$ (0.3 mol %, based on HDI)
Reaction temperature: 80° C.

| Reaction time [hh:mm] | $n_D^{20}$ | HDI conversion [%] | U/T |
|---|---|---|---|
| 01:49 | 1.4542 | 12% | 19.3 |
| 03:49 | 1.4559 | 16% | 15.2 |
| 05:48 | 1.4579 | 20% | 12.6 |
| 21:14 | 1.4648 | 33% | 5.9 |
| 29:27 | 1.4665 | 37% | 4.9 |
| 45:29 | 1.4684 | 40% | 4.1 |

TABLE 4

Catalyst: nbPBu$_2$ (0.6 mol %, based on HDI)
Reaction temperature: 40° C.

| Reaction time [hh:mm] | $n_D^{20}$ | HDI conversion [%] | U/T |
|---|---|---|---|
| 00:59 | 1.4533 | 10% | 14.7 |
| 02:08 | 1.4542 | 12% | 11.2 |
| 04:56 | 1.4559 | 16% | 10.7 |
| 21:41 | 1.4634 | 31% | 7.4 |
| 29:56 | 1.4656 | 35% | 6.2 |
| 72:11 | 1.4697 | 43% | 4.8 |

TABLE 5

Catalyst: nbPDec$_2$ (0.6 mol %, based on HDI)
Reaction temperature: 40° C.

| Reaction time [hh:mm] | $n_D^{20}$ | HDI conversion [%] | U/T |
|---|---|---|---|
| 00:58 | 1.4533 | 10% | 11.0 |
| 03:53 | 1.4550 | 14% | 9.5 |
| 07:47 | 1.4569 | 18% | 8.5 |
| 23:03 | 1.4639 | 31% | 6.3 |
| 30:43 | 1.4668 | 37% | 5.8 |
| 47:13 | 1.4722 | 48% | 4.7 |
| 71:23 | 1.4776 | 59% | 3.9 |

TABLE 6

Catalyst: nb$_2$PDec (0.9/1.4 mol %, based on HDI)
Reaction temperature: 40° C.

| Reaction time [hh:mm] | $n_D^{20}$ | HDI conversion [%] | U/T |
|---|---|---|---|
| 01:06* | 1.4537 | 11% | 27.9 |
| 06:16 | 1.4557 | 15% | 20.6 |
| 21:31 | 1.4591 | 22% | 17.9 |
| 46:16 | 1.4636 | 31% | 11.6 |
| 69:46 | 1.4660 | 36% | 9.4 |
| 93:46 | 1.4674 | 38% | 8.7 |

*up to this point 0.9 mol % of catalyst added, thereafter a further 0.5 mol %

Example 7

Inventive

Catalyst: nbPEt$_2$ (1 mol %, based on HDI); reaction temperature: 30° C.

1050 g of HDI were charged to and degassed in a jacketed vessel with flat-ground joints which was conditioned at 30° C. by means of an external circulation and was fitted with a stirrer, a reflux condenser connected to an inert gas unit (nitrogen/vacuum) and a thermometer. After blanketing with nitrogen, 11.6 g of nbPEt$_2$ were metered in and stirring was carried out at 30° C. for the time indicated in Table 7. The refractive index of the mixture ($n_D^2$) rose to 1.4671. Subsequently the reaction mixture was worked up without deactivation of the phosphine beforehand. Working up took place by vacuum distillation in a thin-film evaporator of the flash evaporator (FE) type, with a preevaporator (PE) connected upstream (distillation data: pressure: 0.08 mbar, PE temperature: 120° C., ME temp.: 150° C., distillation time: 1 h), unreacted monomer being separated off together with the active catalyst as distillate, and the polyisocyanate resin containing uretdione groups being separated off as bottom product (initial run: Example 7–0).

The distillate containing the active catalyst was collected in a second stirring apparatus with flat-ground joints, identical in construction to the first, and immediately after the end of distillation was made up to the starting amount (1050 g) again using freshly degassed HDI. Subsequently stirring was carried out at 30° C. again for the time indicated in Table 7 and following measurement of the refractive index of the reaction mixture it was worked up by distillation as described above (Example 7-A).

This procedure was repeated a total of 18 times (up to Experiment 7-R).

In the course of the experiment, which was carried out over a number weeks, only a very slow decrease in catalytic activity was observed (cf. in this respect Example 8, comparative example), the measure used for which was the slope of the $n_D^{20}$/time curve for each individual experiment (slope=($n_D^{20}$ at beginning of distillation −1.4523)/reaction time). The values obtained for each experiment were placed in relation to the value measured in the starting batch (defined as 100%) (cf. relative reactivity in Table 7 and FIG. 1).

By correlating the refractive index of the crude products with the resin yields realized (=HDI conversion) a calibration curve was plotted (FIG. 2) which was used to calculate the yields of the smaller-scale experiments carried out in Examples 1 to 6 (cf. Example 1–6).

Example 8

Comparative Example

Catalyst: cyclo-Hex-P-n-Hex$_2$ (0.2 mol %, based on HDI); reaction temperature: 40° C.

A procedure similar to that of Example 7 was carried out, with the difference that the catalyst used was 3.6 g of cyclohexyl-di-n-hexylphosphine. The experimental data are set out in Table 8.

As is immediately evident, the uretdione selectivity of the cyclohexyl-di-n-hexyl-phosphine—of comparable conversion—is substantially less than that of the structurally very similar norbornyl derivative of the invention from Example 1.

Figure 1:
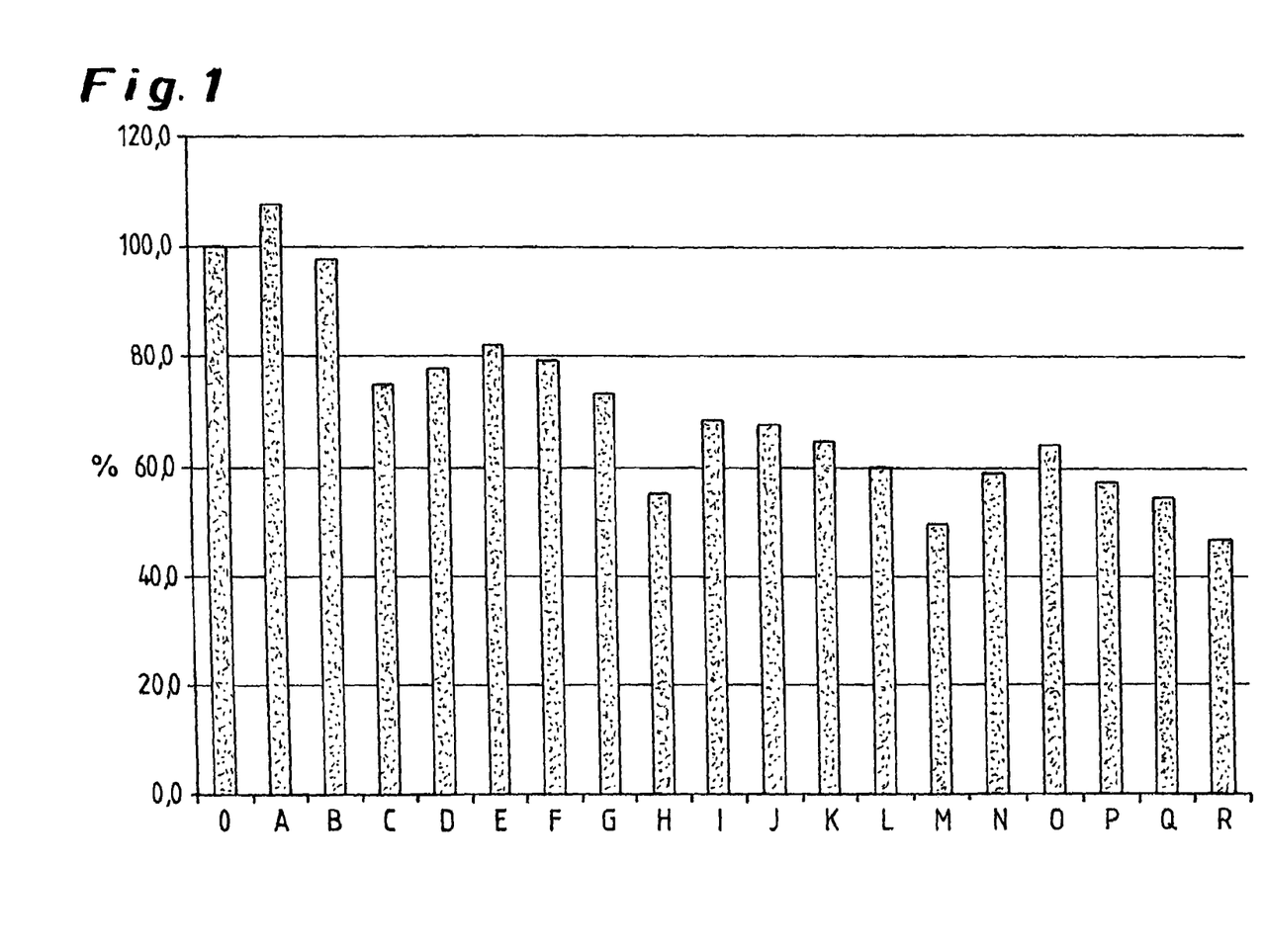
FIG. 1 shows a bar graph depicting the relative reactivity of catalysts according to the invention after different lengths of time.
Figure 3:
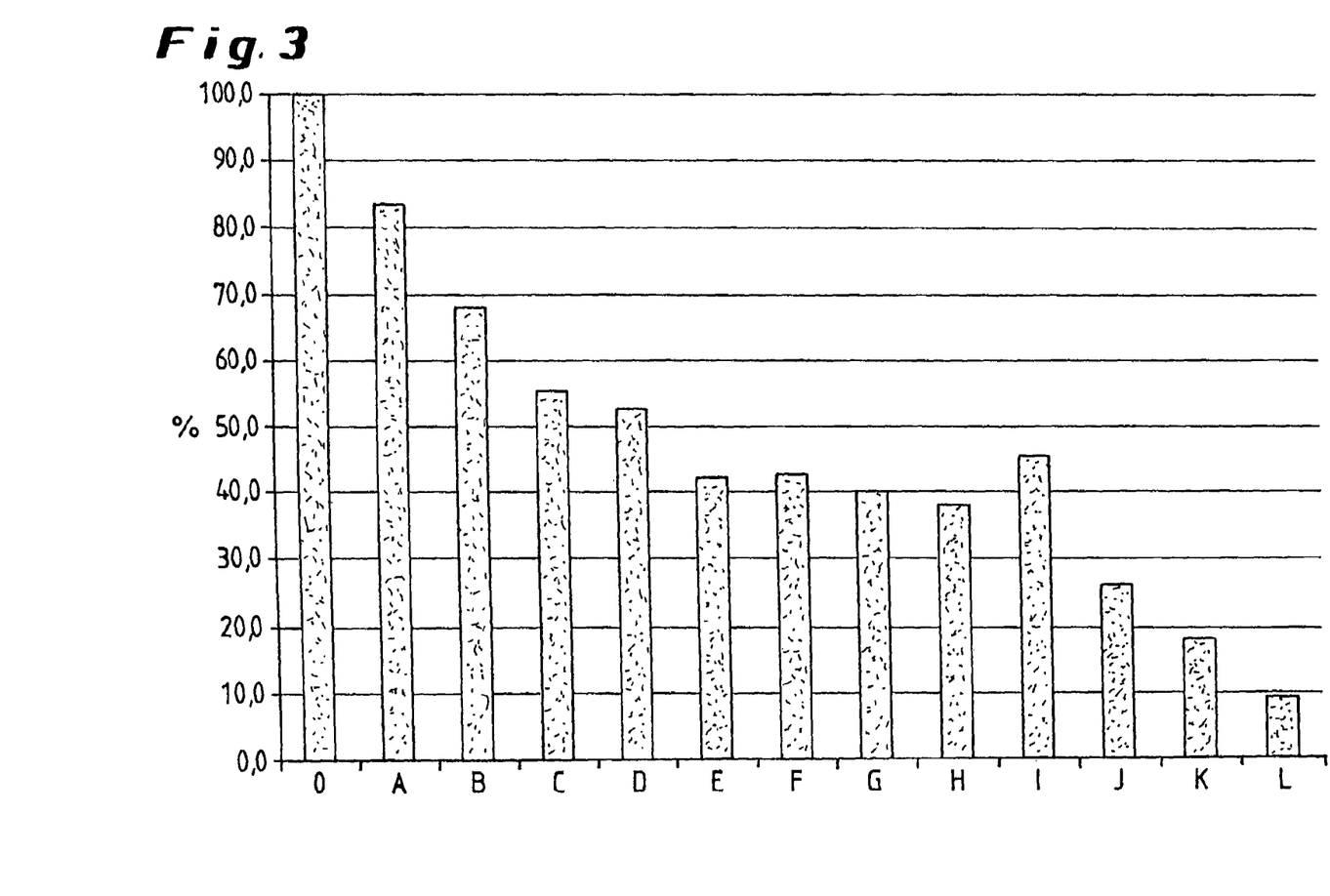
FIG. 3 shows a bar graph depicting the relative reactivity of a prior art catalyst after different lengths of time.

The significantly lower service life of the cyclohexyl-di-n-hexylphosphine as compared with norbornyl-diethylphosphine is very apparent from a comparison of FIGS. 1 and 3.

TABLE 7

Catalyst: nbPEt$_2$ (1 mol %, based on HDI)
Reaction temperature: 30° C., semi-continuous reaction regime

| Ex. 7- | R. time [hh:mm] | $n_D^{20}$ | Rel. reactivity | Yield [%] | NCO content | Viscosity [mPas] at 23° C. | Colour number [APHA] | fr. HDI [%] | U/T |
|---|---|---|---|---|---|---|---|---|---|
| 0 | 24:35 | 1.4671 | 100% | 39.6% | 21.5 | 105 | 27 | 0.10 | 5.3 |
| A | 20:20 | 1.4675 | 107% | 38.6% | 21.3 | 100 | 24 | 0.08 | 6.8 |
| B | 18:45 | 1.4694 | 98% | 46.0% | 20.9 | 130 | 33 | 0.09 | 5.1 |
| C | 69:43 | 1.4843 | 75% | 67.2% | 17.5 | 565 | 24 | 0.10 | 3.6 |
| D | 22:08 | 1.4652 | 78% | 35.2% | 21.8 | 102 | 51 | 0.11 | 5.9 |
| E | 22:43 | 1.4653 | 82% | 35.2% | 22.1 | 85 | 42 | 0.10 | 6.2 |
| F | 22:00 | 1.4640 | 79% | 32.4% | 21.9 | 76 | 40 | 0.10 | 6.8 |
| G | 22:36 | 1.4635 | 73% | 31.5% | 22.1 | 72 | 35 | 0.09 | 7.2 |
| H | 70:59 | 1.4771 | 55% | 58.9% | 18.9 | 218 | 13 | 0.11 | 4.3 |
| I | 22:44 | 1.4630 | 68% | 29.1% | 22.4 | 72 | 27 | 0.10 | 7.1 |
| J | 22:42 | 1.4624 | 68% | 27.9% | 22.4 | 72 | 26 | 0.12 | 7.0 |
| K | 23:26 | 1.4627 | 65% | 27.4% | 22.5 | 68 | 17 | 0.08 | 7.1 |
| L | 28:17 | 1.4633 | 60% | 30.9% | 22.2 | 72 | 11 | 0.10 | 6.9 |
| M | 66:09 | 1.4724 | 50% | 49.2% | 19.5 | 140 | 9 | 0.16 | 5.0 |
| N | 22:50 | 1.4618 | 59% | 26.2% | 22.5 | 68 | 25 | 0.11 | 7.3 |
| O | 21:00 | 1.4618 | 64% | 25.7% | 23.0 | 62 | 24 | 0.25 | 7.4 |
| P | 20:27 | 1.4602 | 58% | 22.1% | 23.1 | 64 | 30 | 0.07 | 8.0 |
| Q | 22:38 | 1.4608 | 55% | 22.7% | 23.1 | 58 | 19 | 0.08 | 7.7 |
| R | 70:31 | 1.4725 | 47% | 50.1% | 20.0 | 136 | 13 | 0.13 | 5.1 |

TABLE 8

Catalyst: cyclo-Hex-P-n-Hex$_2$ (0.2 mol %, based on HDI)
Reaction temperature: 40° C., semi-continuous reaction regime

| Ex. 8- | R time [hh:mm] | $n_D^{20}$ | Rel. reactivity | Yield [%] | NCO content | Viscosity [mPas] at 23° C. | Colour number [APHA] | fr. HDI [%] | U/T |
|---|---|---|---|---|---|---|---|---|---|
| 0 | 18:41 | 1.4643 | 100.0% | 32.8% | 22.4 | 108 | 81 | 0.17 | 3.0 |
| A | 22:58 | 1.4656 | 83.3% | 35.0% | 22.1 | 130 | 40 | 0.16 | 3.1 |
| B | 22:15 | 1.4629 | 68.0% | 29.2% | 22.7 | 112 | 45 | 0.12 | 3.3 |
| C | 22:37 | 1.4609 | 55.3% | 23.9% | 22.8 | 97 | 35 | 0.08 | 3.3 |
| D | 05:26 | 1.4551 | 52.7% | 7.1% | 24.0 | 98 | 43 | 0.09 | 4.3 |
| E | 16:51 | 1.4583 | 42.0% | 14.9% | 23.2 | 100 | 30 | 0.11 | 3.3 |
| F | 23:40 | 1.4598 | 42.7% | 19.3% | 23.0 | 96 | 27 | 0.07 | 3.3 |
| G | 19:52 | 1.4587 | 40.0% | 17.2% | 23.6 | 94 | 17 | 0.08 | 2.0 |
| H | 21:13 | 1.4584 | 38.0% | 12.2% | 23.8 | 90 | 27 | 0.08 | 3.6 |
| I | 03:31 | 1.4553 | 45.3% | 6.8% | 23.9 | 71 | 42 | 0.12 | 6.4 |
| J | 25:35 | 1.4574 | 26.0% | 13.4% | 23.8 | 85 | 40 | 0.13 | 3.7 |
| K | 43:05 | 1.4590 | 18.0% | 16.8% | 22.9 | 96 | 63 | 0.08 | 3.6 |
| L | 56:00 | 1.4565 | 9.3% | 10.7% | 23.9 | 95 | 66 | 0.07 | 3.2 |

Example 9

Inventive

Catalyst: nb$_2$PEt (2.5 mol %, based on HDI); reaction temperature: 30° C.

A procedure similar to that of Example 7 was carried out, with the difference that the catalyst used was nb$_2$PEt. The data are set out in Table 9.

TABLE 9

Catalyst: nb$_2$PEt (2.5 mol %, based on HDI)
Reaction temperature: 30° C., semi-continuous reaction regime

| Ex. 9- | Reaction time [hh:mm] | n$_D$$^{20}$ | Rel. reactivity | Yield [%] | NCO content | Viscosity [mPas] at 23° C. | Colour number [APHA] | fr. HDI [%] | U/T |
|---|---|---|---|---|---|---|---|---|---|
| 0 | 24:13 | 1.4625 | 100.0% | 21.9% | 23.0 | 53 | 91 | 0.13 | 16.0 |
| A | 22:02 | 1.4627 | 97.0% | 19.5% | 23.1 | 56 | 55 | 0.08 | 18.4 |
| C | 20:55 | 1.4620 | 95.5% | 17.9% | 23.2 | 67 | 57 | 0.10 | 19.8 |
| D | 22:08 | 1.4622 | 91.0% | 17.9% | 23.1 | 60 | 43 | 0.07 | 18.9 |
| E | 22:05 | 1.4622 | 89.6% | 17.9% | 23.1 | 65 | 43 | 0.09 | 19.6 |
| F | 22:22 | 1.4620 | 85.1% | 17.8% | 23.1 | 61 | 59 | 0.08 | 19.2 |
| G | 22:02 | 1.4625 | 88.1% | 18.7% | 23.2 | 64 | 54 | 0.11 | n.d. |
| H | 22:07 | 1.4624 | 86.6% | 18.8% | 23.2 | 69 | 40 | 0.09 | n.d. |
| I | 70:18 | 1.4712 | 74.6% | 42.3% | 20.8 | 95 | 24 | 0.08 | 15.0 |
| J | 21:34 | 1.4618 | 85.1% | 17.4% | 23.1 | 62 | 79 | 0.08 | n.d. |
| K | 22:22 | 1.4615 | 79.1% | 15.7% | 23.2 | 66 | 50 | 0.07 | n.d. |
| L | 22:11 | 1.4617 | 79.1% | 17.1% | 23.3 | 68 | 60 | 0.31 | n.d. |
| M | 28:08 | 1.4630 | 77.6% | 21.0% | 23.0 | 67 | 27 | 0.07 | n.d. |
| N | 64:09 | 1.4692 | 70.1% | 38.3% | 21.1 | 81 | 21 | 0.06 | 16.9 |
| O | 24:30 | 1.4613 | 70.1% | 17.5% | 23.0 | 65 | 48 | 0.07 | n.d. |
| P | 24:20 | 1.4616 | 76.1% | 11.9% | 22.3 | 98 | 68 | 0.08 | n.d. | n.d.: not determined

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of dimerizing isocyanates comprising reacting said isocyanates in the presence of phosphines containing at least one directly phosphorus-attached bicyclic, cycloaliphatic radical.

2. A process for dimerizing isocyanates, comprising reacting a mixture that includes
   a) at least one organic isocyanate having an NCO functionality $\geq 2$,
   b) a catalyst comprising at least one phosphine containing at least one directly phosphorus-attached bicyclic, cycloaliphatic radical, and
   c) optionally solvents.

3. The process for dimerizing isocyanates according to claim 2, wherein the dimerization is carried out at a temperature of 0–150° C. to a conversion of the NCO groups of from 5 to 90% and thereafter is terminated.

4. The process for dimerizing isocyanates according to claim 2, wherein component a) includes aliphatic, cycloaliphatic or araliphatic di- or polyisocyanates having an NCO functionality $\geq 2$.

5. The process according to claim 2, wherein the mixture further comprises one or more additives selected from the group consisting of anti-oxidants, light stabilizers, and catalysts for the NCO—OH reaction.

6. The process for dimerizing isocyanates according to claim 3, wherein component a) includes aliphatic, cycloaliphatic or araliphatic di- or polyisocyanates having an NCO functionality $\geq 2$.

* * * * *